United States Patent
O'Heeron et al.

(10) Patent No.: US 6,783,516 B2
(45) Date of Patent: Aug. 31, 2004

(54) TROCAR

(75) Inventors: Peter T. O'Heeron, Houston, TX (US); Patrick C. Newlin, Houston, TX (US)

(73) Assignee: NeoSurg Technologies, Inc., Houston, TX (US)

( * ) Notice: Subject to any disclaimer, the term of this patent is extended or adjusted under 35 U.S.C. 154(b) by 182 days.

(21) Appl. No.: 10/008,189

(22) Filed: Nov. 13, 2001

(65) Prior Publication Data

US 2003/0093101 A1 May 15, 2003

(51) Int. Cl.$^7$ .................. A61M 13/00; A61M 5/00; A61M 5/178
(52) U.S. Cl. ................. 604/256; 604/65; 604/167.03
(58) Field of Search .................. 604/248, 164.11, 604/264, 167.06, 167.04, 167.03, 167.01, 167.02, 533, 256, 905

(56) References Cited

U.S. PATENT DOCUMENTS

| | | | | |
|---|---|---|---|---|
| 4,820,409 A | * | 4/1989 | Lowsky et al. | 137/854 |
| 5,820,606 A | * | 10/1998 | Davis et al. | 604/164.11 |
| 5,827,228 A | * | 10/1998 | Rowe | 604/167.02 |
| 6,066,117 A | * | 5/2000 | Fox et al. | 604/249 |
| 6,116,277 A | * | 9/2000 | Wilcox et al. | 137/614 |
| 6,276,661 B1 | * | 8/2001 | Laird | 251/61.1 |

\* cited by examiner

Primary Examiner—Brian L. Casler
Assistant Examiner—Roz Grafoorian
(74) Attorney, Agent, or Firm—Jackson Walker L.L.P.; Clarence E. Eriksen; Bryan P. Galloway

(57) ABSTRACT

A trocar is disclosed which comprises a housing assembly having an upper end and a lower end and a cannula assembly attached to the lower end of the housing assembly to define an axial bore therethrough. The disclosed trocar also includes an obturator for sliding engagement in the bore. The housing assembly includes an access port formed on the upper end which is axially aligned with the bore of the trocar. Communication via the access port of the housing is regulated by a flapper valve having a closed position and a range of open positions. The flapper valve comprises a metal flapper door having a male/female configuration formed around the protrusion. In the closed position, the protrusion of the flapper door engages the male/female configuration of both door and port mesh resulting in a metal-to-metal seal across the access port. The metal-to-metal seal provides enhanced resistance to mechanical, heat, and chemical wear encountered during surgical and sterilization operations.

5 Claims, 3 Drawing Sheets

TROCAR

BACKGROUND OF THE INVENTION

1. Field of the Invention

The present invention relates to surgical instruments known as trocars which are used in endoscopic surgery to pierce or puncture an anatomical cavity to provide communication with the cavity during a surgical procedure. More particularly, the present invention relates to an improved flapper valve assembly for communication with bore of the trocar.

2. Description of the Prior Art

Endoscopic surgery is an essential method of performing surgical operations and has become the surgical procedure of choice, because of its patient care advantages over "open surgery." More particularly, a form of endoscopic surgery is laparoscopic surgery. A significant advantage of laparoscopic surgery over open surgery is the decreased post-operative recovery time. In most instances, a patient is able to leave the hospital within hours after laparoscopic surgery has been performed, whereas with open surgery, a patient requires several days of hospital care to recover. Additionally, laparoscopic surgery achieves descreased incidents of post-operative abdominal adhesions, decreased post-operative pain, and enhanced cosmetic results.

Conventionally, a laparoscopic surgical procedure begins with the insulation of the abdominal cavity with carbon dioxide. The introduction of this gas into the abdominal cavity lifts the abdominal wall away from the internal viscera. The abdominal wall is then penetrated with a device known as a trocar, which includes a housing assembly, a cannula assembly attached to the housing assembly to form a bore through the trocar, and a piercing element called an obturator. The obturator slides through an access port formed on the upper end of the housing assembly and through the bore of the trocar. After insertion of the trocar through the abdominal wall of the patient, the obturator is removed by the surgeon while leaving the cannula or tube protruding through the body wall. Laparoscopic instruments can then be inserted through the cannula to view internal organs and to perform surgical procedures.

However, once the obturator is removed from the bore of the housing, it is necessary to obstruct the access port so that the carbon dioxide gas introduced into the abdominal cavity of the patient is contained. Traditionally, a flapper valve having a removable non-metallic seal is used to regulate communication via the access port. For example, the trocar disclosed in U.S. Pat. No. 6,238,407 uses a flapper valve with a removable rubber or silicon seal to insure the access port is tightly secured once the obturator is removed.

While the removable rubber or silicon seal provides an excellent means to secure the access port during laparoscopic surgery, the use of such non-metallic seals have undesirable results as well. Non-metallic seals are not as resilient to mechanical, chemical, and thermal wear as the surrounding metal components of the trocar. Therefore, non-metallic seals must be disposed of and replaced after operational use and wear due to chemical and high temperature sterilization procedures. Maintenance and replacement procedures require the trocar to be disassembled and reassembled thereby expending valuable time and resources.

Accordingly, it would be desirable to have a trocar with a flapper valve and sealing means being fabricated entirely of durable metal and providing a metal-to-metal seal for the access port without the use of non-metallic sealing agents. This novel and useful result has been achieved by the present invention.

SUMMARY OF THE INVENTION

In accordance with the present invention, a trocar is provided which comprises a metal housing assembly having an upper and lower ends. An access port is formed in the upper end of the housing assembly. A sealing, metal protrusion is shaped to fit the access port of the housing and meshes with its mating seal component. Communication via the access port is regulated by a flapper valve sub-assembly. The flapper valve comprises a metal flapper door having a protrusion formed thereon and a recessed ring formed around the protrusion. The flapper door has a "closed" position where the access port is obstructed and a range of "open" positions where communication via the access port is unobstructed. In the "closed" position, the configuration of the flapper door contacts and seals against the access port's mating metal seal configuration in the trocar housing. This results in a consistent, normal wear resistant, metal to metal seal across the mating surfaces of the access port and flapper valve mechanism. Furthermore, the flapper valve incorporates a device for biasing the flapper door in the "closed and sealed" position and provides required force to achieve desired pressure seal.

A trocar in accordance with the present invention further comprises a cannula assembly attached to the lower end of the housing assembly to define a bore therethrough. The cannula assembly is axially aligned with the access port of the housing assembly.

A trocar in accordance with the present invention also comprises an obturator assembly for sliding engagement in the bore. The obturator has a piercing end which slides into the access port of the housing assembly and rotates the flapper valve to the open position. With communication established through the access port, the obturator may slide through the bore of the trocar defined by the cannula assembly and penetrate the abdominal wall of the patient. Once the obturator is removed from the trocar, the flapper valve resets to the closed position to obstruct communication through the bore of the trocar.

DESCRIPTION OF SPECIFIC EMBODIMENT

Figure 1:
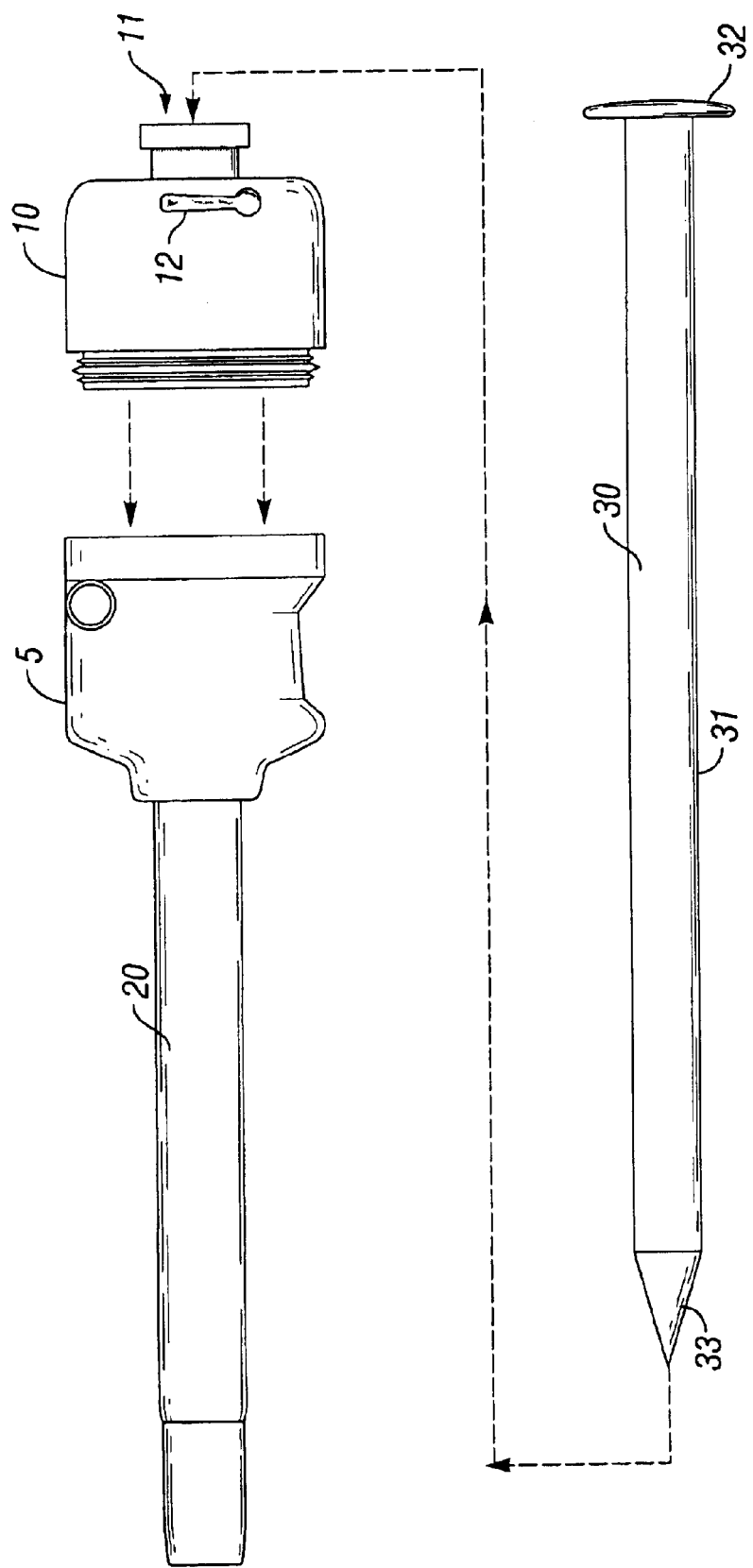
FIG. 1 is an exploded perspective view of an embodiment of a trocar in accordance with the present invention.

With reference to FIG. 1, a trocar 5 in accordance with the present invention comprises a housing assembly 10 to which is attached a cannula assembly 20. The cannula assembly 20 is a hollow tube, and when attached to the housing assembly 10, a bore is defined through the trocar 5. An access port 11 is exists the housing assembly 10 such that the access port and the bore defined by the cannula assembly 20 are axially aligned.

Still with reference to FIG. 1, a trocar 5 in accordance with the present invention also includes an obturator assembly 30 having a shaft 31 with an arcuate-shaped cap 32 at the proximal end of the shaft and a piercing tip 33 at the distal end of the shaft. The obturator assembly 30 slides in the bore that is defined by the combination of housing assembly 10 and cannula assembly 20.

Figure 2A:
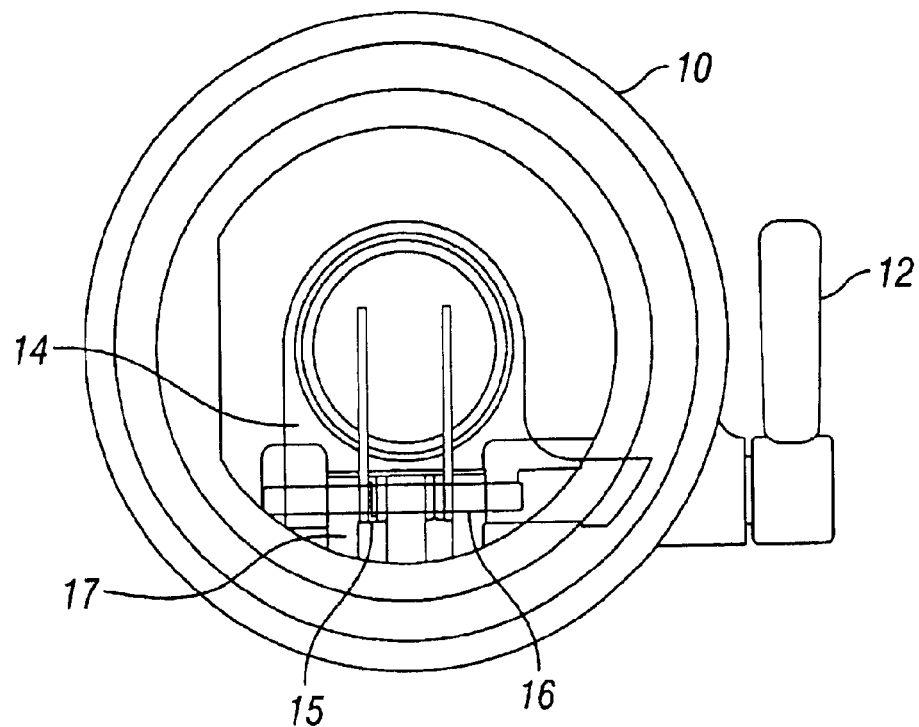
FIG. 2A is a axial section view of a trocar in accordance with the present invention with flapper valve in closed position.
Figure 2B:
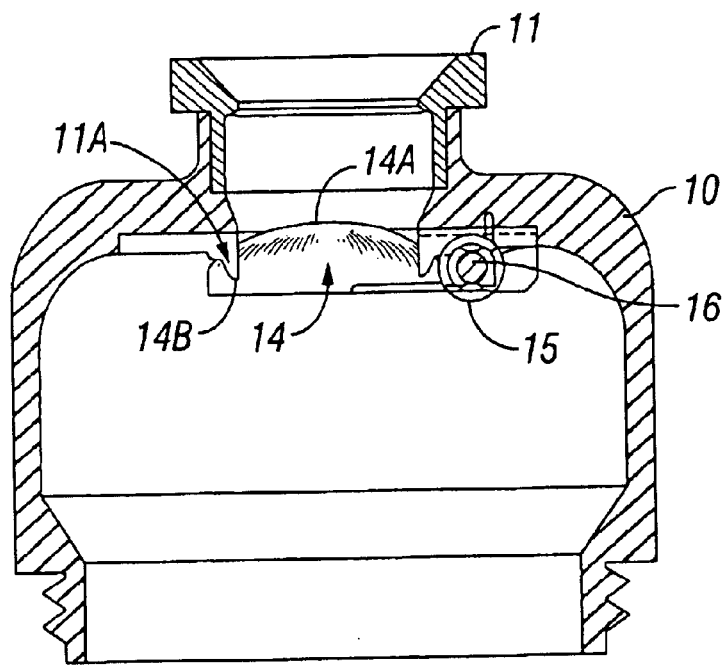
FIG. 2B is a lateral section view of a trocar in accordance with the present invention with flapper valve in closed position.
Figure 3A:
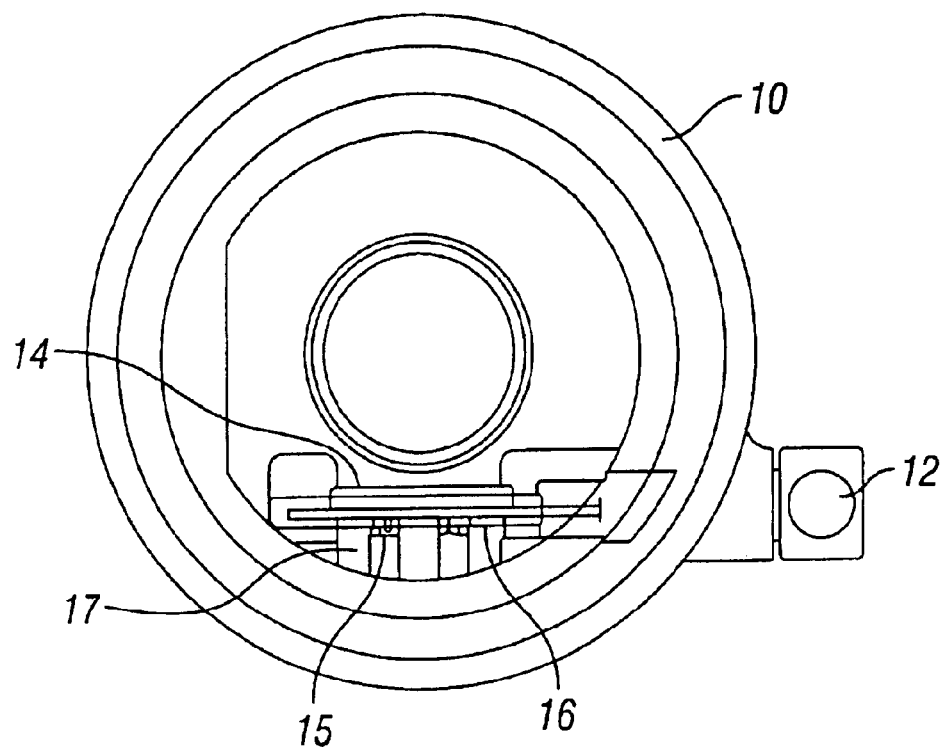
FIG. 3A is a axial section view of a trocar in accordance with the present invention with flapper valve in open position.
Figure 3B:
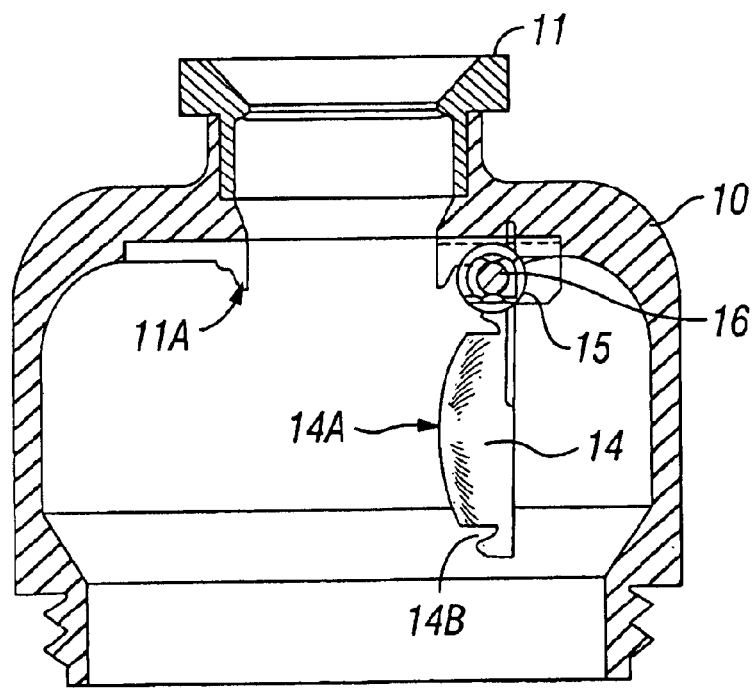
FIG. 3B is a lateral section view of a trocar in accordance with the present invention with flapper valve in open position.

With reference to FIGS. 2A and 2B, and 3A and 3B, a trocar in accordance with the present invention includes a flapper valve door 14 for regulating communication through the access port 11. The flapper valve door 14 comprises a protrusion 14A and a recessed ring 14B formed around the protrusion. Recessed ring 14B is thus a circular recess which is formed in the flapper valve door and which defines a ring around the protruding element 14A. circular mating ring 11A is formed around the access port 11 and extends toward the flapper valve door 14. The circular mating ring 11A is thus a protruding ring which is formed around the access port of the housing and which extends toward the flapper valve door 14. The flapper valve door 14 is rotatably connected to the housing assembly 10 by pivot mounts 17 flapper pin 16. The flapper valve door 14 is rotatable between a closed position (FIGS. 2A and 2B) and an open position (FIGS. 3A and 3B). Resistance mechanisms 15, such as torsion springs or compression springs, bias the flapper valve door 14 in the closed position. A manual flapper door actuator 12, which is attached to the flapper valve sub-assembly 16, is provided for manual rotation of the flapper valve door 14 between the closed position and range of open positions.

Still with reference to FIGS. 2A and 2B, and 3A and 3B, the flapper valve door 14, protrusion 14A, recessed ring 14B, and circular mating ring 11A are all fabricated from durable metal. Preferably these components are fabricated from hardened, scratch resistant, highly polished stainless steel.

With reference to FIGS. 2A and 2B, in the closed position, the protrusion 14A of flapper valve door 14 engages access port 11, and circular mating ring 11A engages recessed ring 14B. This engagement produces a metal-to-metal seal which obstructs communication to the bore of the trocar via the access port 11.

With reference to FIGS. 3A and 3B, in the open position, the protrusion 14A and recessed ring 14B of flapper valve door 14 rotate out of engagement with access port 11 and circular mating ring 11A respectively. The access port 11 is unobstructed and communication is established with the bore of the trocar 5.

In operation, a trocar in accordance with the present invention is used to facilitate laparoscopic surgical procedures performed on a patient. With reference to FIGS. 1, 2A and 2B, and 3A and 3B, prior to insertion of trocar 5, the abdominal cavity of the patient in insufflated with carbon dioxide gas to lift the abdominal wall away from the internal viscera. An obturator 31 is slid into bore of the trocar 5 via an access port 11 formed in housing assembly 10 thereby moving flapper valve door 14 to an open position against the resistance mechanism 15. The obturator 31 is then used to pierce the abdominal wall of the patient such that cannula assembly 20 penetrates into the abdominal cavity. Once the trocar 5 is inserted through the abdominal wall of the patient, the obturator 31 is removed while leaving tube of cannula assembly 20 protruding through the abdominal wall. As the obturator 31 is removed from the bore of the trocar 5, the double torsion springs 15 reset the flapper valve door 14 into the closed position to seal the access port 11 and prevent the carbon dioxide gas from escaping the abdominal cavity. Laparoscopic instruments are then inserted through the cannula assembly 20 to view internal organs and to perform surgical procedures.

The advantages of a trocar in accordance with the present invention are provided by the metal-to-metal flapper valve seal in lieu of prior art rubber and silicon seals and include enhanced flapper valve durability to resist the effects of mechanical wear, and damaging chemical and high temperature sterilization procedures. Other advantages of the present invention will be apparent to those skilled in the art who have the benefit of the present specification.

What is claimed is:

1. A trocar, comprising:
   a. a housing assembly having an upper end and a lower end, said housing having an access port formed at the upper end;
   b. a cannula assembly attached to the lower end of the housing assembly and defining an axial bore therethrough, said axial bore being aligned with the access port;
   c. an obturator assembly for sliding engagement through the axial bore defined by the cannula assembly via the access port of the housing; and
   d. a flapper valve attached to the housing assembly having a closed position where the access port is obstructed by the flapper valve and an open position where the access port is unobstructed by the flapper valve such that communication is established with the axial bore defined by the cannula assembly, said flapper valve comprising:
      (i.) a flapper door which is fabricated from metal and which has a protruding element formed thereon for engagement with the access port of the housing and a circular recess formed therein defining a ring around the protruding element, said protruding element having a diameter approximately equal to the diameter of the access port of the housing;
      (ii.) a protruding ring which is fabricated from metal and which is formed around the access port of the housing and extending toward the flapper door, said protruding ring being formed to mate with the circular recess of the flapper door when the flapper valve is in the closed position; and
      (iii.) a resistance mechanism for biasing the flapper door of the flapper valve in the closed position.

2. The trocar of claim 1, wherein the resistance mechanism is one or more double torsion springs.

3. The trocar of claim 1, wherein the resistance mechanism is one or more compression springs.

4. The trocar of claim 1, wherein the valve assembly further comprises a flapper door handle connected to external wall of the housing and being manually rotatable such that the flapper valve moves between the closed position and the range of open positions.

5. The trocar of claim 1, wherein the flapper door, protruding element, and protruding ring are fabricated from metal.

* * * * *